US009717671B2

(12) United States Patent
Richelle et al.

(10) Patent No.: US 9,717,671 B2
(45) Date of Patent: Aug. 1, 2017

(54) COMPOSITION FOR IMPROVING SKIN, HAIR AND COAT HEALTH CONTAINING FLAVANONES

(75) Inventors: Myriam Richelle, Savigny (CH); Elizabeth Offord-Cavin, Poliez-Pittet (CH); Karlheinz Bortlik, Syens (CH); Isabelle Bureau-Franz, Morges (CH); Gary Williamson, Mezieres (CH); Inge Lise Nielsen, Montreaux (CH); Heike Steiling, Lausanne (CH); Angus Moodycliffe, Pully (CH)

(73) Assignee: Nestec S.A., Vevey (CH)

( * ) Notice: Subject to any disclaimer, the term of this patent is extended or adjusted under 35 U.S.C. 154(b) by 1008 days.

(21) Appl. No.: 10/596,468

(22) PCT Filed: Dec. 17, 2004

(86) PCT No.: PCT/EP2004/014416
§ 371 (c)(1),
(2), (4) Date: Jun. 14, 2006

(87) PCT Pub. No.: WO2005/058255
PCT Pub. Date: Jun. 30, 2005

(65) Prior Publication Data
US 2007/0129428 A1    Jun. 7, 2007

(30) Foreign Application Priority Data
Dec. 18, 2003    (EP) .................... 03029183

(51) Int. Cl.
| | |
|---|---|
| *A61K 36/752* | (2006.01) |
| *A61K 8/60* | (2006.01) |
| *A61K 31/352* | (2006.01) |
| *A61Q 5/00* | (2006.01) |
| *A61Q 19/00* | (2006.01) |
| *A23L 33/105* | (2016.01) |
| *A61Q 5/02* | (2006.01) |
| *A61Q 17/04* | (2006.01) |
| *A61Q 19/08* | (2006.01) |

(52) U.S. Cl.
CPC ............ *A61K 8/602* (2013.01); *A23L 33/105* (2016.08); *A61K 31/352* (2013.01); *A61Q 5/00* (2013.01); *A61Q 19/00* (2013.01); *A23V 2002/00* (2013.01); *A61K 2800/92* (2013.01); *A61Q 5/02* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 4,049,798 | A | * | 9/1977 | Bottomley .................. 424/736 |
| 5,587,176 | A | * | 12/1996 | Warren et al. .............. 424/443 |
| 5,849,786 | A | * | 12/1998 | Bidel et al. .................. 514/458 |
| 6,159,475 | A | * | 12/2000 | Olguin ......................... 424/731 |
| 6,365,199 | B1 | | 4/2002 | Olguin |
| 2003/0125264 | A1 | * | 7/2003 | Malik ............................ 514/27 |
| 2003/0166583 | A1 | | 9/2003 | Yoa-Pu Hu et al. |
| 2007/0129428 | A1 | | 6/2007 | Richelle et al. |

FOREIGN PATENT DOCUMENTS

| | | |
|---|---|---|
| CN | 1229638 | 9/1999 |
| DE | 10111045 A1 | 9/2002 |
| EP | 0461627 A2 | 12/1991 |
| EP | 0774249 | 5/1997 |
| EP | 0774249 A2 | 5/1997 |
| EP | 1750651 | 2/2007 |
| JP | 63066110 | 3/1988 |
| JP | 09252746 A * | 9/1997 |
| JP | 2002029975 | 1/2002 |

OTHER PUBLICATIONS http://web.archive.org/web/20010719165229/http://www.nbizz.com/longevityclinic/listings/23.html.*
http://170.107.206.70/drug_info/nmdrugprofiles/nutsupdrugs/hes_0295.shtml.*
http://dermnetnz.org/systemic/xeroderma-pigmentosum.html.*
Ameer et al., Flavanone absorption after naringin, hesperidin, and citrus administration, 1996, Clin Pharm Ther, 60, 34-40.*
Global Herbal Supplies 2010 http://www.globalherbalsupplies.com/herpes/symptoms.htm.*
Abstract XP-002283597, Cosmetic Material Contain Methyl-Hesperidin—Useful for Preventing Sunburn to Skin and Hair Decolouration, Application No. JP 1988-122604.
Abstract XP-002283596, Nutrition Supplement Food for Treating Baldness, Etc.—Contains Tahibo Extracts and Natural Mineral, Application No. JP 1997-530127.
Abstract XP-002283595, Free Radical Scavenger Comprises Eriocitrin and Vitamin C, Useful in Food Drink, Medicine or Cosmetics Applications, Application No. JP 2002-248238.
Abstract XP-002283594, Refreshing Shampoo Prepared From Pomelo Exocarp or Leaf, Application No. JP 2000-024196.
Communication from the European Patent Office dated Jun. 11, 2012 enclosing third party observation concerning patentability of EP1750651.
Yoshioka et al. "Synergistic Effects of Vitamins P (Hesperidin) and C as Citrus-Rejuvenation-Directed Inner Cosmetics on Skin Rejuvenation" Bio Industry, vol. 20, No. 5, 2003, pp. 19-29.

(Continued)

*Primary Examiner* — Terry A McKelvey
*Assistant Examiner* — Catheryne Chen
(74) *Attorney, Agent, or Firm* — K&L Gates LLP

(57) ABSTRACT

The present invention pertains to a composition for preventing, decreasing and/or treating skin and hair/coat disorders, such as is effected by inflammatory reactions, environmental factors, ageing or cancer. In particular, the present invention relates to the use of flavanones compounds or their derivatives in nutritional, cosmetic or pharmaceutical compositions for improvement of human or pet animal skin and coat conditions.

8 Claims, 4 Drawing Sheets

(56) References Cited

OTHER PUBLICATIONS

Abstract—JP Application No. 1997-530127—"Nutrition supplement food for treating baldness, etc.—contains tahibo extracts and natural mineral" XP002263530.
Key Attributes of TKDL—Utraj—3 pages—XP003030650.
Key Attributes of TKDL—Sharbati Lemoon—3 pages—XP003030651.
Key Attributes of TKDL—Sharbat-e-gurhal A—3 pages—XP003030655.
Key Attributes of TKDL—Sharaab-as-saaleheen—3 pages—XP003030652.
Key Attributes of TKDL—Maa-ul-Jubn—3 pages—XP003030653.
Key Attributes of TKDL—Maajoon—3 pages—XP003030654.

* cited by examiner

COMPOSITION FOR IMPROVING SKIN, HAIR AND COAT HEALTH CONTAINING FLAVANONES

The present invention pertains to a composition for preventing, decreasing and/or treating skin and hair/coat disorders or damages, such as is effected by inflammatory reactions, environmental factors, ageing or cancer. In particular, the present invention relates to the use of flavanones compounds or their derivatives in nutritional, cosmetic or pharmaceutical compositions for improvement of human or pet animal skin and coat conditions.

BACKGROUND OF THE INVENTION

The most prominent epithelial tissue in living beings is the skin, which represents the largest organ in the organism. The system of skin integument, which comprises the epidermis, dermis and the stratum corneum, correlates with those of internal organs and concurrently interacts with the surroundings. Being the interface between the environment and organism itself, the skin is heavily influenced by external factors and also variable parameters of the organism's inner system. The skin's regulative mechanisms need, therefore, always be active to induce systemic changes necessary to maintain normal pathological events concerning skin integument morphology and activities.

A great deal of processes assuring the adequate consumption of increased affluence of energetic and plastic substances according to the skin's needs become guarantors of morphological and functional stability of skin structures. So, the state of integuments determines the realization of metabolic processes necessary for skin cell viability and activity leading to the presence of healthy skin peculiarities such as barrier function, elasticity, turgor properties, humidity, pigmentation etc.

During the lifetime of a living being different signs, characteristic of ageing, appear on the skin or hair, with the principal clinical signs being the appearance of fine lines and deep wrinkles which increase or are accentuated with age, loss of hair, reduced hair density, glossiness, color, oiliness, fiber diameter, etc.

These signs of ageing are even promoted by exposure of the skin and hair to exogenous influences, such as e.g., UV-radiation, pollutants, free radicals or chemical substances.

In the art several means have been proposed to prevent destructive effects of environment or ageing on skin epithelial cells. For example, means to prevent skin deterioration or ageing is to provide compounds scavenging free radicals. In this respect EP 0 761 214 discloses singlet oxygen quenchers comprising aniline derivatives and difurfuryl amine derivatives, which are reported to reduce the oxidative stress to the skin.

Although there is a great diversity of active compounds for ameliorating skin and hair or coat health, there still exists a need in the art to provide new active compounds. In particular, an object of the present invention is to provide compositions that may be used over a long period of time by humans or pets, and susceptible to be provided in the form of a nutritional supplement, for example a nutritional composition.

SUMMARY OF THE INVENTION

In a first aspect, the present invention relates to a nutritional, cosmetic or pharmaceutical composition for human or pets, which contains as active compound, at least one flavanone compound or its derivatives, or a mixture thereof, in an efficient amount to prevent, treat or alleviate skin, hair and/or coat disorders and ameliorate skin, hair and coat health.

In another aspect, the invention provides the use of at least one flavanone or its derivatives or mixtures thereof, as active compound in the preparation of a nutritional, cosmetic or pharmaceutical composition intended for preventing or treating skin, hair and/or coat disorders, thus ameliorating skin health conditions in humans or pets.

The composition according to the present invention may be in the form of a complete nutritional formula, a dietary supplement to be orally administered to a human or an animal, or a compound for pharmaceutical use.

Administering to a human or pet animal, a food composition as described above, results in an improved skin health, e.g., on photoprotection, hydration, dryness, firmness, thickness, elasticity, oiliness, regular pigmentation, immunity or hair and coat health, e.g., improving hair and coat gloss, hair density, color, oiliness, ameliorating hair fiber diameter, sebum production, glossiness and preventing hair and coat loss. Also, the composition according to the present invention is administered to a human or an animal, for ameliorating antioxidant status, barrier function, to prevent or modulate oxidative status, sebum production or composition, or to reduce signs of ageing. It also helps to reduce risks of cancer or inflammation.

Additional features and advantages are described herein, and will be apparent from the following Detailed Description and the figures.

DETAILED DESCRIPTION OF THE INVENTION

Figure 1:
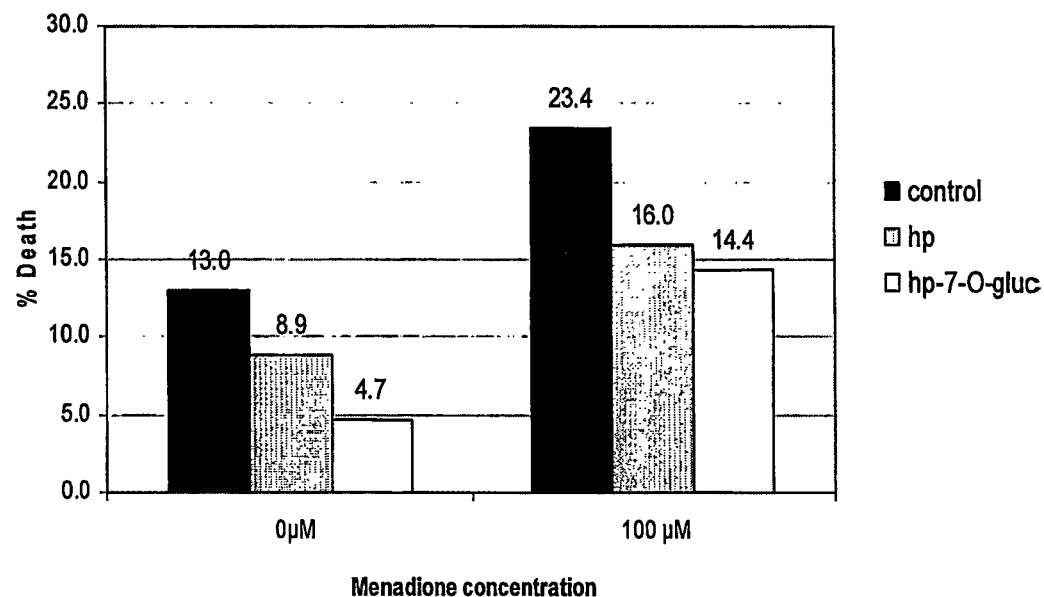
FIG. 1: HaCat cells were incubated with 10 µM hesperetin (hp, red bars) or low 10 µM hesperetin-7-O-glucuronide (hp-7-O-gluc, yellow bars) or equal amounts of DMSO as a control (blue bars) and treated with or without menadione for additional 5 h. The supernatant was analyzed for lactate dehydrogenase (LDH) activity and results were expressed relative to cells which were lysed with Triton X-100® before analysis (100% death).

According to the first object, the invention provides a nutritional, cosmetic or pharmaceutical composition for oral administration for human or pets, which contains as active compound, at least one flavanone compound or its derivatives, or a mixture thereof, in an efficient amount to prevent, treat or alleviate skin, hair and/or coat disorders or damages and thus ameliorate skin, hair and coat health.

The flavanone compounds of interest are natural glycosides that can be found principally in fruits from the genus Citrus, such as orange, lemon, bitter orange, grapefruit, for example or in a lesser extend in other vegetables. They are present in majority in the peel of the fruit, but also in large amounts in the pulp and thus also in citrus fruit juice. The compounds according to the present invention may be isosacuranetin, naringin, hesperidin, or eriodictyol, poncirin, neoeriocitrin, for example, and their derivatives selected from their aglycone forms, chalcone forms, glycosylated forms or methylated forms. Also, their sulfated or glucuronidated forms which are found as product of metabolism in blood are used.

In a last aspect, derivatives may be obtained by several processes known in the art, such as enzymatic treatments. For example, glucose-7-hesperetin is prepared by rhamnosidase or hesperidinase treatment.

The flavanone compound or derivatives according to the invention may be included in any composition suitable for administering the substance to an individual, in particular a food composition, a cosmetic composition or a pharmaceutical composition.

In a preferred embodiment, a food composition for human consumption is prepared. This composition may be a nutritional complete formula, a dairy product, a chilled or shelf stable beverage, soup, a dietary supplement, a meal replacement, and a nutritional bar or a confectionery. The composition may be selected from the group consisting of milk, or fermented milk products, such as e.g. yogurt, curd, cheese, milk based fermented products, ice-creams, milk based powders, infant formulae, cereal products and fermented cereal based products, beverages, mineral water, chocolate or pet food containing at least a flavanone compound or one of its derivatives. The nutritional supplement for oral administration may be in capsules, soft capsules, tablets, pastes or pastilles, gums, or drinkable solutions or emulsions. Methods for preparing them are common knowledge.

As described above, flavanones compounds are found naturally in Citrus fruits, in particular in oranges, lemons and grapefruit, in their peel or pulp. Accordingly, in a first aspect, the nutritional composition may be in the form of a juice of such fruits or in the form of a concentrate. Thus, the nutritional composition may be in the form of any food product, in particular any beverage, citrus juice or any other extract from peel or pulp of citrus fits.

In another embodiment, a usual food product may be enriched with the flavanones, preferably in the form of citrus extract. For example, a fermented milk, a yoghurt, a fresh cheese, a renneted milk, a confectionery bar, breakfast cereal flakes or bars, drinks, milk powders, soy-based products, non-milk fermented products or nutritional supplements for clinical nutrition. In particular, a process for preparing an extract enriched if flavanones, in particular hesperidin, from orange and lemon is described in U.S. Pat. No. 2,400,693 and U.S. Pat. No. 2,442,110, respectively.

According to a further aspect, flavanones compounds to be included in the specification may be synthetically produced.

A nutritional composition according to the present invention may comprise the flavanone compounds, its derivatives or mixtures thereof in an amount adapted to a daily oral administration, and of from about 0.01 mg to 1 g, preferably from about 0.1 mg to 800 mg, more preferably from 10 mg to 800 mg of the aglycone equivalent of the flavanone compound.

The flavanones according to the invention may be used either alone or in association with other active compounds such as vitamin C, vitamin E (tocopherols and tocotrienols), carotenoids (carotenes, lycopene, lutein, zeaxanthine, beta-cryptoxanthine, etc.) ubiquinones (e.g., CoQ10), catechins (e.g., epigallocatechin gallate), coffee extracts containing polyphenols and/or diterpenes (e.g., kawheol and cafestol), extracts of chicory, ginkgo biloba extracts, grape or grape seed extracts rich in proanthocyanidins, spice extracts (e.g., rosemary), soy extracts containing isoflavones and related phytoestrogens and other sources of flavonoids with antioxidant activity, fatty acids, e.g., n-3 fatty acids, prebiotic fibers, probiotic microorganisms, taurine, resveratrol, aminoacids, selenium and precursors of gluthathione, for example.

In another embodiment, a pharmaceutical compositions can be administered for prophylactic and/or therapeutic treatments. In therapeutic applications, compositions are administered to a patient already suffering from a disease, as described herein under, in an amount sufficient to cure or at least partially arrest the symptoms of the disease and its complications. An amount adequate to accomplish this is defined as "a therapeutically effective dose". Amounts effective for this will depend on the severity of the disease and the weight and general state of the patient.

In prophylactic applications, compositions according to the invention are administered to a patient susceptible to or otherwise at risk of a particular disease. Such an amount is defined to be "a prophylactic effective dose". In this use, the precise amounts again depend on the patient's state of health and weight. Preferably, for humans the pharmaceutical composition according to the present invention comprises an amount of flavanone compounds, its derivatives or mixture thereof as described above, for a daily administration, from about 0.01 mg to 500 mg. When administered daily to pets, the composition may comprise from 1 mg to 500 mg of the aglycone equivalent of flavanone compounds.

The compounds of the invention are preferably administered with a pharmaceutical acceptable carrier, the nature of the carrier differing with the mode of administration, for example parenteral, intravenous, oral and topical (including ophthalmic) routes.

It will be appreciated that the skilled person will, based on his own knowledge select the appropriate components and galenic form to target the active compound to the skin or hair taking into account the route of administration which may be by way of injection, topical application, intranasal administration, administration by implanted or transdermal sustained release systems, and the like.

The objective substance may also be formulated in a cosmetic product, such as lotions, shampoos, creams, sunscreens, after-sun creams, sun-blocker, anti-ageing creams and/or ointments. It will be appreciated that the present cosmetic products will contain a mixture of different ingredients known to the skilled person, ensuring a fast penetration of the objective substance into the skin and preventing degradation thereof during storage.

It will be understood that the concept of the present invention may likewise be applied as an adjuvant therapy assisting in presently used medications. Since the compounds of the present invention may easily be administered together with food material special clinical food may be applied containing a high amount of the objective substances. It will be clear that on reading the present specification together with the appending claims the skilled person will envisage a variety of different alternatives to the specific embodiments mentioned herein.

In principle, the compounds according to the present invention may be used for the treatment and/or prevention of damages in the skin which are produced by a stress situation e.g., by means of a chemical, biological or a physical stress, e.g., by exposure to oxidants or carcinogens, exposure to bacteria, viruses, fungi, lipids derived from surrounding cells and/or microbes, or exposure to LTV-irradiation.

Consequently, the substances and/or compositions according to the present invention may be utilized for treating and or preventing damages of the skin, in particular actinic and ageing damages of the skin such as dryness, actinic keratoses, irregular pigmentation (notably comprising freckling, lentigines, guttate hypomelanosis and persitent hyperpigmentation), wrinkling (notably comprising fine surface lines and deep furrows), stellate pseudoscars, elastosis, inelasticity, telangiectasia, venous lakes, purpura, comedones, sebaceous hyperplasia, acrochordon, cherry angiogema, seborrhea keratosis, lentigo, basal cell carcinoma and squamous cell carcinoma, skin burning and/or blistering, epidermal hyperplasia, inflammation, immune suppression, and cancer, e.g., non-melanoma and melanoma skin cancers. They have also particular benefits on hair and coat, such as an improved hair or coat density, fiber diameter, color, oilness, glossiness, sebum production and a helps to prevent hair or coat loss.

The effect of a food supplementation in flavanones compounds or its derivatives according to the present invention, on skin of humans or pets, can be measured by using conventional methods including minimal erythemal dose (MED), colorimetry, transepidermal water loss, DNA repair (e.g., p. 53), measure of interleukines and proteoglycans production, or collagenase activity, barrier function or cell renewal.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The following examples illustrate the invention in more detail without restricting the same thereto.

Example 1: Mineral Water Supplemented with Flavanone

A mineral water is prepared by adding hesperetin-7-glucose, in an amount of 0.01 mg to 200 mg per liter, estimating that the average consumption is of about 1 liter per day.

Example 2: Cosmetic for Oral Administration

A composition in the form of a hard capsule has the following formulation:

|  | mg per capsule |
|---|---|
| Compound | |
| Hespéridine (hesperetin equivalent) | 250 |
| Excipient for the core | |
| Cellulose microcristalline | 70 |
| Encompress ™ | 60 |
| Stéarate de Magnésium | 3 |
| Silice colloïdale anhydre | 1 |
| Coating agent | |
| Gum-lac | 5 |
| Talc | 61 |
| Sucrose | 250 |
| polyvidone | 6 |
| titanium dioxide | 0.3 |
| coloring agent | 5 |

The composition can administered to the individual in an amount of 2 to 3 capsules daily.

Example 3: Canned Pet Food and Supplement

A mixture is prepared from 73% of poultry carcass, pig lungs and beef liver (ground), 16% of wheat flour, 7% of water, 2% of dyes, flavours, vitamins, and inorganic salts. This mixture is emulsified at 12° C. and extruded in the form of a pudding which is then cooked at a temperature of 90° C. It is cooled to 30° C. and cut in chunks. 45% of the chunks are mixed with 55% of a sauce prepared from 98% of water, 1% of dye and 1% of guar gum. Tinplate cans are filled and sterilized at 125° C. for 40 min.

As a supplement to be mixed with the pet-food before serving, additional packaging in sachet form with 50 mg of hesperetin equivalent, in the form of Citrus extract is provided. This is supplied as a supplement with removably attached to the can, together with feeding directions.

Example 4: Functional Food

A food supplement was prepared by mixing or blending fructooligosaccharide with inulin in the proportions by weight of about 70% fructooligosaccharide to about 30% inulin and adding 500 mg of hesperetin equivalent. The resulting prebiotic mixture may be added or blended with any suitable carrier, for example a fermented milk, a yogurt, a fresh cheese, a renneted milk, a confectionery bar, breakfast cereal flakes or bars, a drink, milk powder, soy-based product, non-milk fermented product or a nutritional supplement for clinical nutrition.

Example 5

Material and Methods
Cytotoxicity Assay

Human immortalized keratinocytes (HaCaT) were incubated with 10 μM hesperetin, 10 μM hesperetin-7-O-glucuronide or equal amounts of DMSO as a negative control for 16 h and 1 h before challenge. Cells were then treated with 100 μM menadione, a xenobiotic which generates reactive oxygen species intracellularly. Non-menadione treated cells were used as a positive control. After 5 h the supernatant was analysed for lactate dehydrogenase (LDH) activity as a measure for cell death using the CytoTox 96 non-radioactive cytotoxicity assay (Promega, USA).

Skin Samples

Figure 2:
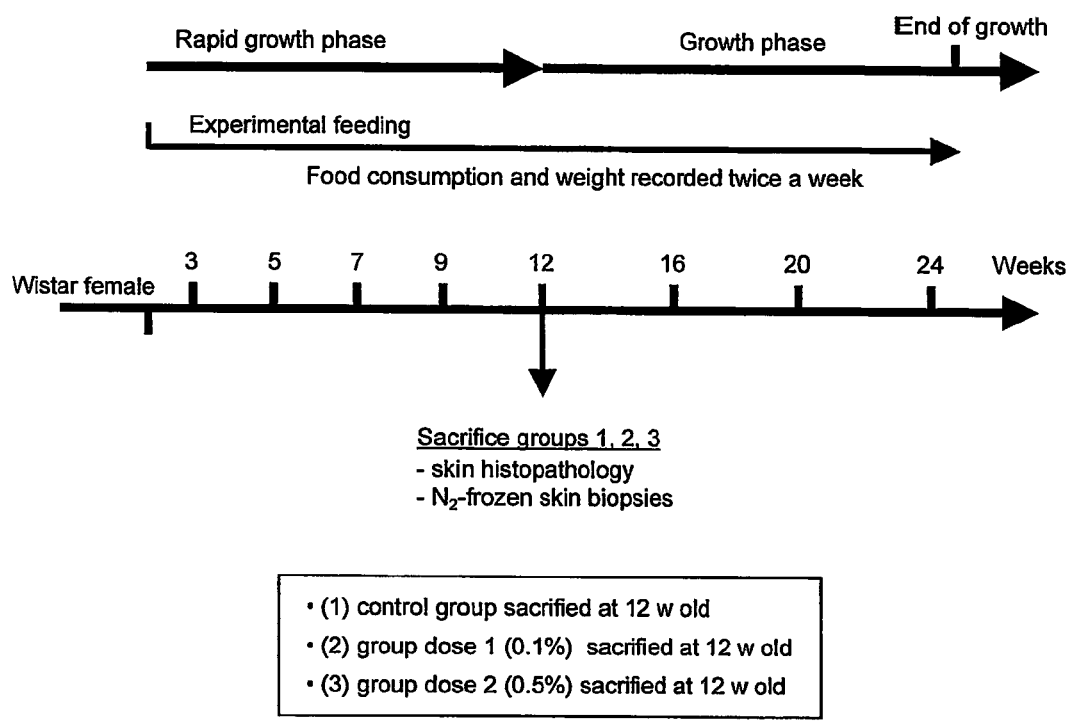
FIG. 2: Chart representing the experimental set-up of the hesperidin growth trial.

Rat skin biopsies were obtained from the Heperidin growth trial (FIG. 2). Dorsal skin was excised, one part was fixed in 4% PFA and paraffin embedded, one part was cryo-preserved and another part was immediately frozen in liquid nitrogen.

Histology

Paraffin Sections

Rat skin was dissected and fixed for 4 days in 4% paraformaldehyde in PBS (pH 7.4) at 4° C. and embedded in paraffin using a Leica Microsystem embedding apparatus. The tissues were washed in PBS and saline (0.9% NaCl) and dehydrated by passing them through saline solutions with increasing ethanol concentrations: 30 min each in 30%, 50%, 70%, 90%, 99%, 100% and an additional hour in 100%. Tissue samples were incubated twice for 30 min in xylene, followed by 2-3 h and 3 h incubations in paraffin wax at 60° C. 6 μm thick paraffin sections were cut using a Leica Microtome. Sections were de-waxed 5 min in xylene and dehydrated by passing them through a series of solutions with decreasing ethanol concentrations: 1 min each in 100%, 96%, 90%, 80%, 70%, and 50% ethanol. Finally, they were transferred into destilled water and stained.

Hematoxylin/Eosin Staining

Rehydrated sections were stained for 45 sec in Mayer's hematoxylin solution, rinsed with the following series of solution for 1 min each: destilled water, tap water, destilled water and 70% ethanol. After staining 10 sec in eosin solution (1% (v/v) in 90% ethanol) sections were rinsed in 90% and 100% ethanol. Following two 10 min incubations in xylene, coverslips were mounted with Eukitt® quick-hardening mounting medium and air-dried for 2 h at room temperature.

RNA Methods

General Directions for Working with RNA

For experiments with RNA, sterile plastic or baked glass vessels (180° C. for at least 8 h) have been used. All surfaces were cleaned with RNase ZAP® decontamination solution prior use, including pipetmen, and aerosol resistant tips were used only.

Equipment

ABI PRISM® 7000HT Sequence Detection System, Applied Biosystems, USA

ABI PRISM® 7000 RT-PCR software, Applied Biosystems, USA

PCR Cycler, e.g., PTC-100™ Programmable Thermal Controller, MJ Research Inc., USA Agilent 2100 bioanalyzer, Agilent Technologies, USA Fluorescence Plate Reader, e.g., SpectraFLUOR® Plus F 129005, Tecan, USA Multifuge 3S, Heraeus with special buckets for MFC centrifugation, Kendro Laboratory Products, Switzerland Cooling Centrifuge, e.g., Centrifuge 5417R, Eppendorf, Germany Reagents ToTally RNA™ Kit (Art. No. 1910), Ambion, USA Lysing Matrix D (Art. No. 6913-100), Q BIOgene, France RNA 6000 Nano Assay (Art. No. 5065-4475 and 5065-4476), Agilent Technologies, USA Assays-on-demand (20× stock, Applied Biosystems, USA)

RNase ZAP® (Art. No. 9780), Ambion, USA

Nuclease-free water (ddH20, Art. No. 9939), Ambion, USA

Milli-Q filtered water (0.22 μM, ddH2O)

Ethanol, GR for analysis (Art. No. 02860), Fluka

Dulbecco's phosphate buffered saline (PBS, Art. No. D8537), Sigma, USA

β-Mercaptoethanol (Art. No. M7522), Sigma, USA

RiboGreen® RNA Quantitation Kit (Art. No. R-11490), Molecular Probes, USA

SUPERase-In™ RNase Inhibitor (20U/μl, Art. No. 2694), Ambion, USA

SuperScript™ II RNase H⁻ reverse transcriptase (200U/μl, Art. No. 18064-014), Invitrogen, USA First-strand buffer (5×): 250 mM NaCl, 0.1 mM EDTA, 1 mM DTT, 0.1% (v/v) NP-40, 50% (v/v) glycerol, included with SuperScript™ II RNase H⁻ reverse transcriptase Dithiothreitol (DTT, 1 mM), included with SuperScript™ II RNase H⁻ reverse transcriptase 2'-Deoxyadenosin-5'-triphosphate (dATP, 100 mM, Art. No. 272050), Amersham Biosciences, England 2'-Deoxycytidine-5'-triphosphate (dCTP, 100 mM, Art. No. 272060), Amersham Biosciences, England 2'-Deoxyguanosine-5'-triphosphate (dGTP, 100 mM, Art. No. 272070), Amersham Biosciences, England 2'-Deoxythymidin-5'-triphosphate (dTTP, 100 mM, Art. No. 272080), Amersham Biosciences, England pd(N)$_6$ Random hexamer (Art. No. 27-2166-01), Amersham Biosciences, England TaqMan® Universal PCR Master Mix (Art. No. PN4304437), Applied Biosystems, USA

TABLE 1

Assays-on-demand used (Assay ID), including Gene names, genes symbols and reference sequences.

| Gene name | Gene symbol | Reference sequence | Assay ID |
|---|---|---|---|
| interleukin 6 | Il6 | NM_012589 | Rn00561420_m1 |
| CD1d1 antigen | Cd1d1 | NM_017079 | Rn_00567162_m1 |
| proliferating cell nuclear antigen | Pcna | NM_022381 | Rn00574296_g1 |
| glyceraldehyde-3-phosphate dehydrogenase | Gapd | NM_017008 | Rn99999916_s1 |

RNA Extraction

Skin samples were homogenized with Lysing Matrix D, total RNAs were extracted using the ToTally RNA™ Kit following the manufacturer's instructions. RNA was eluted with 40 μl of nuclease-free water.

RNA Quantification

The quantification was performed using the Ribogreen® RNA quantitation Kit on 96-well plates and a fluorescence microplate reader according to the manual. Measurements were done in duplicate. The samples were diluted either 1:680 or 1:3400 in a final volume of 100 μl 1×TE buffer. Dilutions of the ribosomal RNA in a concentration of 1, 0.5, 0.1, 0.02, 0 μg/ml were used as standards. Integrity of 1 μl RNA was controlled using RNA 6000 Nano Assay.

Reverse Transcription

All manipulations were done on ice. 2 μl pd(N)$_6$ random hexamers and 1 μl dNTP (10 mM) were added to 2 μg RNA in nuclease-free water in a final volume of 12 μl. After 5 min incubation at 65° C., samples were immediately placed on ice and quickly centrifuged. Then, 4 μl of 5× first strand buffer, 2 μl of dithiothreitol, 1 μl of RNase inhibitor and 1 μl of reverse transcriptase SuperScript™ II RNase H⁻ were added (final volume 20 μl). The reverse transcription reaction was performed in a PCR cycler using the following temperature program: activation of the enzyme: 10 min at 25° C.; reverse transcription reaction: 60 min at 42° C.; inhibition of the enzyme: 20 min at 70° C. The sample was then kept in the freezer at −20° C. until further use.

Real-Time Polymerase Chain Reaction

The real-time PCR was performed according to the TaqMan® method in 96 well plates (96WP) using assays-on-demand primer and probes. Analysis was done in triplicate using a master mix (3.5×) which contained 43.7 μl TaqMan® 2× Universal PCR master mix, 4.4 μl assays-ondemand primers and probes, 21.9 μl nuclease-free water and 17.5 μl cDNA (87.5 ng=25 ng per replicate). Triplicates of 25 μl master mix were loaded on a 96 well ABI PRISM® reaction plate, covered with a transparent optical adhesive cover and centrifuged three times at 2000 rpm for 1 min or until all air-bubbles had been removed. The PCR reaction was then performed in the ABI PRISM® 7000 Sequence Detection System using the following temperature program: activation of the enzyme: 2 min at 50° C.; denaturation: 10 min at 95° C. and 40 cycles target amplification: 15 sec annealing at 95° C. and 1 min extension at 60° C. The analysis of the amplification plots was done using the ABI PRISM® software Baseline adjustments were done individually (116: 15-25, Cdldl: 10-20, Pcna: 15-25; Gapd: 6-15), whereas thresholds were set manually at 0.2 for all primers. The resulting Ct values were exported into Microsoft Excel for further analysis.

Statistical Analysis

Data were analysed by ANOVA.

Results and Discussion

In vitro experiments using immortalized keratinocytes (HaCat) demonstrated that treatment with hesperetin (hp) and hesperetin-7-O-glucuronide (hp-7-0-gluc) is reducing cell death under normal culture conditions. The protective effect of hp and hp-7-O-gluc was even more pronounced in cells challenged with menadione, a xenobiotic which increases intracellular levels of reactive oxygen species (ROS). Moreover, hp-7-O-gluc, the main metabolite of hesperidin in blood, seems to be more potent compared to hp, the aglycone (FIG. 1).

Figure 3:
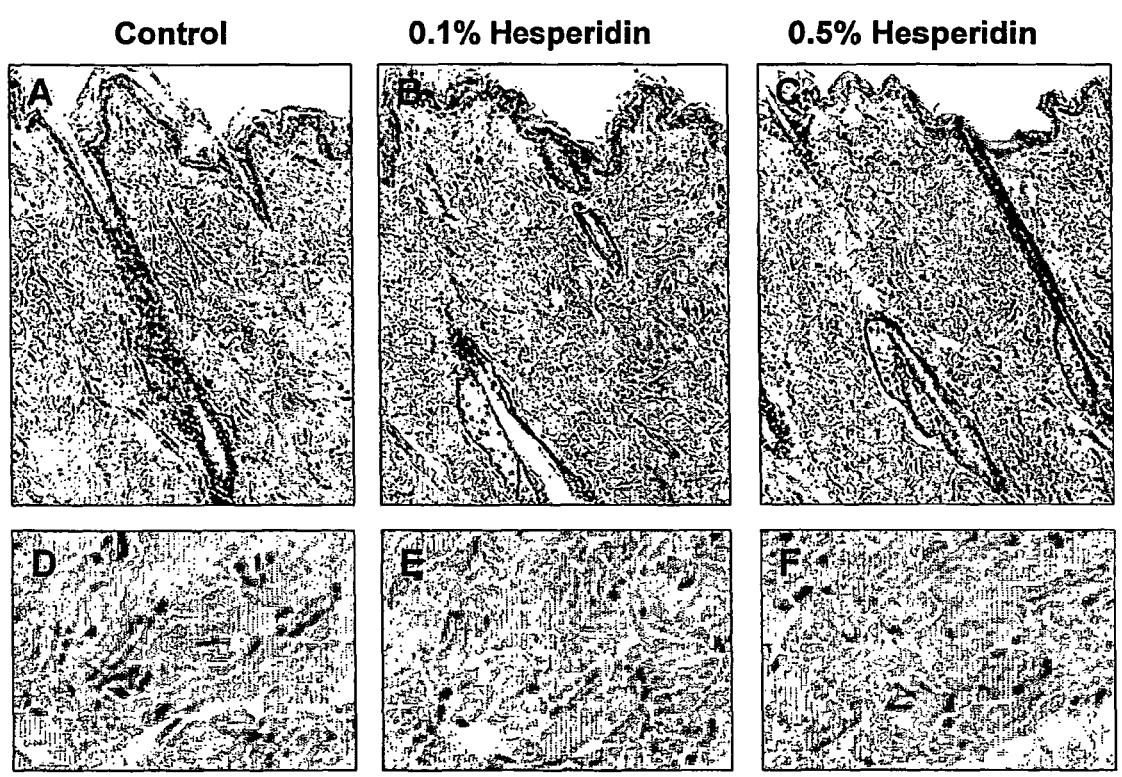
FIG. 3: Histopathological analysis of rat skin supplemented with hesperidin. 6 µm paraffin sections were de-waxed, stained with hematoxylin/eosin and mounted. Representative images in two magnifications are shown for the control group (A and D) and the groups supplemented with hesperidin (0.1%: B and E, 0.5% C and F).
Figure 4:
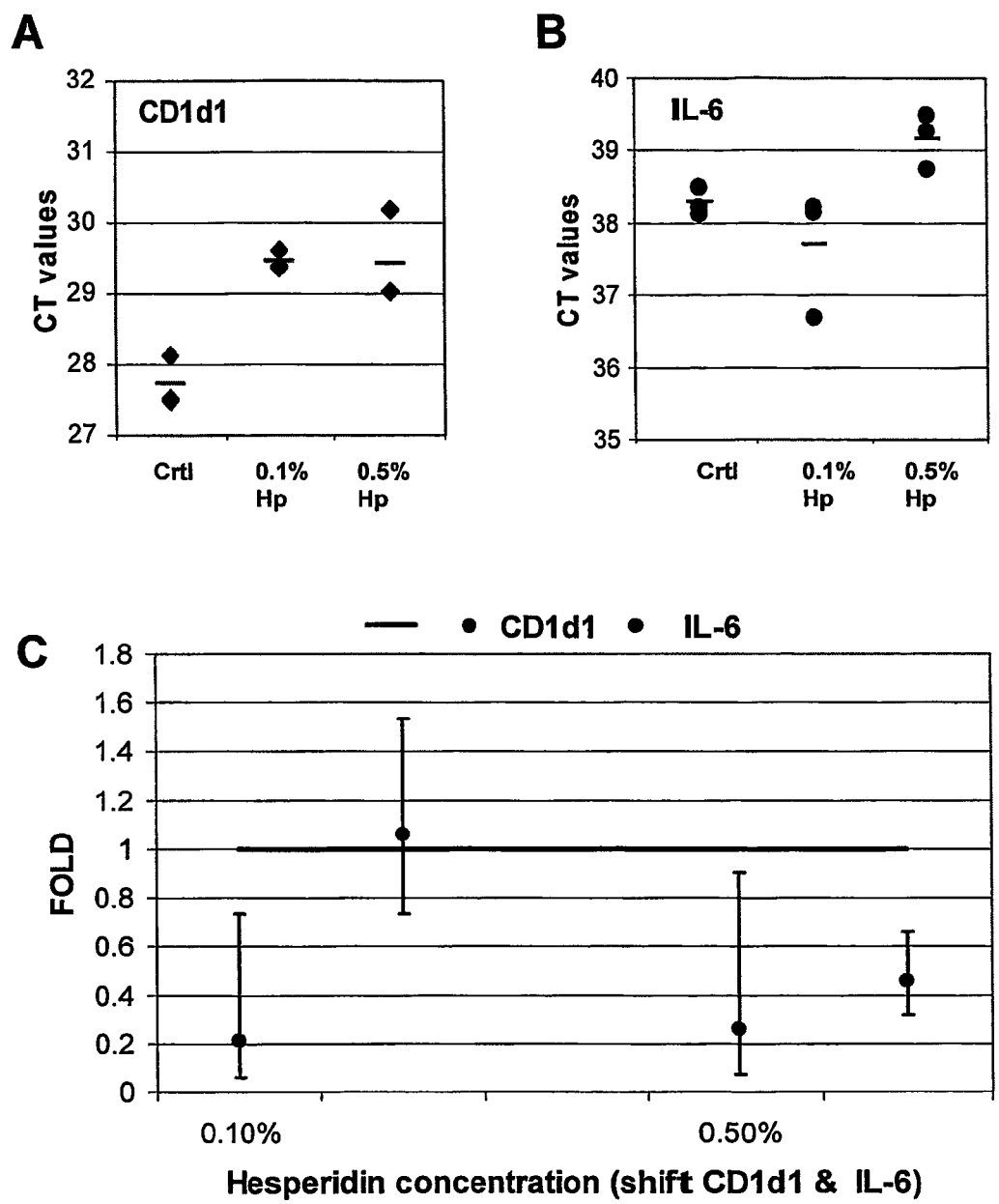
FIG. 4: Real-time PCR analysis of total RNA isolated from rat skin fed either a control diet (ctrl) or a hesperidin-supplemented diet (0.1% Hp, 0.5% Hp) for the expression of CD1d1 and interleukin 6 (IL-6). Samples were analyzed in 3 pools containing 4 rats each and obtained Ct values are shown for CD1d1 in A and IL-6 in B. Dots represent averages of technical triplicates, bars the total average per group. Fold changes in relative expression of the supplementation compared to control diet and relative to a housekeeping gene are shown in C. The control diet was set to 1 fold and is represented by a thick line. Confident intervals were calculated using ANOVA.

The protective effect of hesperidin was further investigated in an animal intervential trial using growing female wistar rats. After weaning, rats were randomized in 3 groups with 12 animals each and supplemented with either a control diet, or a hesperidin supplemented diet using two different doses (0.1% and 0.5%). At the age of 12 weeks rats were sacrificed and skin tissue was used for skin histology and mRNA analysis (FIG. 2). Histopathological analysis of the skin revealed a reduced number of inflammatory cells in animals fed the hesperidin diet. Representative images are shown in FIG. 3 (3A+D (control) vs. 3B+E (0.1% hesperidin) vs. 3C+F (hesperidin)). These histological observations could be confirmed at the mRNA level. Rats fed 0.5% hesperidin showed significantly reduced levels of IL-6, an inflammatory cytokine (FIG. 4A+C). In addition CDldl mRNA levels were significantly decreased in both groups supplemented with hesperidin (FIG. 4B+C).

These data clearly demonstrate cytoprotective and anti-inflammatory properties of orally administrated hesperidin for skin.

The invention claimed is:

1. A method for improving at least one skin characteristic of a human or pet animal, wherein the at least one skin characteristic is selected from the group consisting of regular pigmentation, reduced risks of inflammation, and reduced signs of ageing, the method comprising:
   orally administering a composition comprising hesperetin-7-0-glucuronide as an active ingredient to a human or pet animal requiring improvement in the at least one skin characteristic, the hesperetin-7-0-glucuronide present in an amount from 0.01 mg to 1.0 g of aglycone equivalent of the hesperetin-7-0-glucuronide per daily dose.

2. The method according to claim 1, wherein the composition is selected from the group consisting of a nutritional composition and pharmaceutical composition.

3. The method according to claim 1, wherein the human or pet animal suffers a skin disorder or damage produced by a situation selected from the group consisting of ageing, chemical stress, biological stress, physical stress, exposure to oxidants, carcinogens, bacteria, fungi, lipids derived from surrounding cells, microbes, and exposure to UV-irradiation.

4. The method according to claim 1, wherein the composition is administered to improve hair and coat gloss, hair density, color, oiliness, to ameliorate hair fiber diameter, and sebum production.

5. The method according to claim 1, wherein the composition is administered to improve cytoprotection of the skin or to reduce inflammation of the skin.

6. The method according to claim 1, wherein the human or pet animal is in need of improvement in skin pigmentation.

7. The method according to claim 1, wherein the human or pet animal is in need of a reduced risk of skin inflammation.

8. The method according to claim 1, wherein the human or pet animal is in need of reduced signs of ageing.

* * * * *